United States Patent [19]

Englehaupt

[11] Patent Number: 5,739,916
[45] Date of Patent: Apr. 14, 1998

[54] APPARATUS AND METHOD FOR DETERMINING THE CONCENTRATION OF SPECIES IN A SUBSTANCE

[75] Inventor: Darell E. Englehaupt, Madison, Ala.

[73] Assignee: University of Alabama at Huntsville, Huntsville, Ala.

[21] Appl. No.: 567,995

[22] Filed: Dec. 4, 1995

[51] Int. Cl.$^6$ .................................................. G01N 21/25
[52] U.S. Cl. ........................................... 356/414; 356/70
[58] Field of Search ........................... 356/45, 402–411, 356/425, 436, 410, 414, 326, 328, 325, 323, 330–334, 70; 250/227.23, 227.11; 385/12, 13

[56] References Cited

U.S. PATENT DOCUMENTS

| | | |
|---|---|---|
| 3,995,168 | 11/1976 | Neuscheler et al. . |
| 4,193,694 | 3/1980 | Smith ......................... 356/425 X |
| 4,225,230 | 9/1980 | Dostoomian et al. ............ 356/45 |
| 4,570,069 | 2/1986 | Gager . |
| 4,635,473 | 1/1987 | Hochstein . |
| 4,672,216 | 6/1987 | Pitt et al. . |
| 4,699,509 | 10/1987 | Kamiya et al. . |
| 4,786,171 | 11/1988 | LeFebre et al. ............ 356/436 X |
| 4,845,469 | 7/1989 | Benda . |
| 4,864,870 | 9/1989 | Payne et al. . |
| 4,912,687 | 3/1990 | Treeby . |
| 5,021,665 | 6/1991 | Ames . |
| 5,043,697 | 8/1991 | Ayabe et al. . |
| 5,071,527 | 12/1991 | Kauffman . |
| 5,076,397 | 12/1991 | Yamada . |
| 5,089,780 | 2/1992 | Megerle . |
| 5,196,898 | 3/1993 | Tamura et al. . |
| 5,257,539 | 11/1993 | Gale et al. . |
| 5,262,732 | 11/1993 | Dickert et al. . |
| 5,296,843 | 3/1994 | Wohlstein et al. . |
| 5,300,218 | 4/1994 | Graiff et al. . |

FOREIGN PATENT DOCUMENTS

| | | | |
|---|---|---|---|
| 0054827 | 4/1982 | Japan | ......................... 356/319 |

OTHER PUBLICATIONS

Francis T.S. Yu et al., "Application of a fiber–speckle hologram to fiber sensing," *Applied Optics*, vol. 33, No. 22, pp. 5202–5203 (Aug. 1, 1994).

*Primary Examiner*—K. Hantis
*Attorney, Agent, or Firm*—Bell Seltzer Intellectual Property Law Group of Alston & Bird LLP

[57] ABSTRACT

An instrument and a method are provided for determining the concentration of at least one species in a substance. The instrument and method can be used to identify and distinguish among various degrees of contamination of motor oil, diesel fuel, and hydraulic fluid by water, ethylene glycol, wear particles, and loss of anti-oxidants. The instrument includes a broad band light source, such as a tungsten filament incandescent lamp, which is very inexpensive and reliable. A fiber optic link is provided to a detector that receives and discriminates among optical spectral transmissions through the fiber optic. Discrimination circuitry is provided for evaluating the transmission and providing a readout that indicates the quality of the fluid. The instrument is suitable for in situ determination of oil quality.

26 Claims, 12 Drawing Sheets

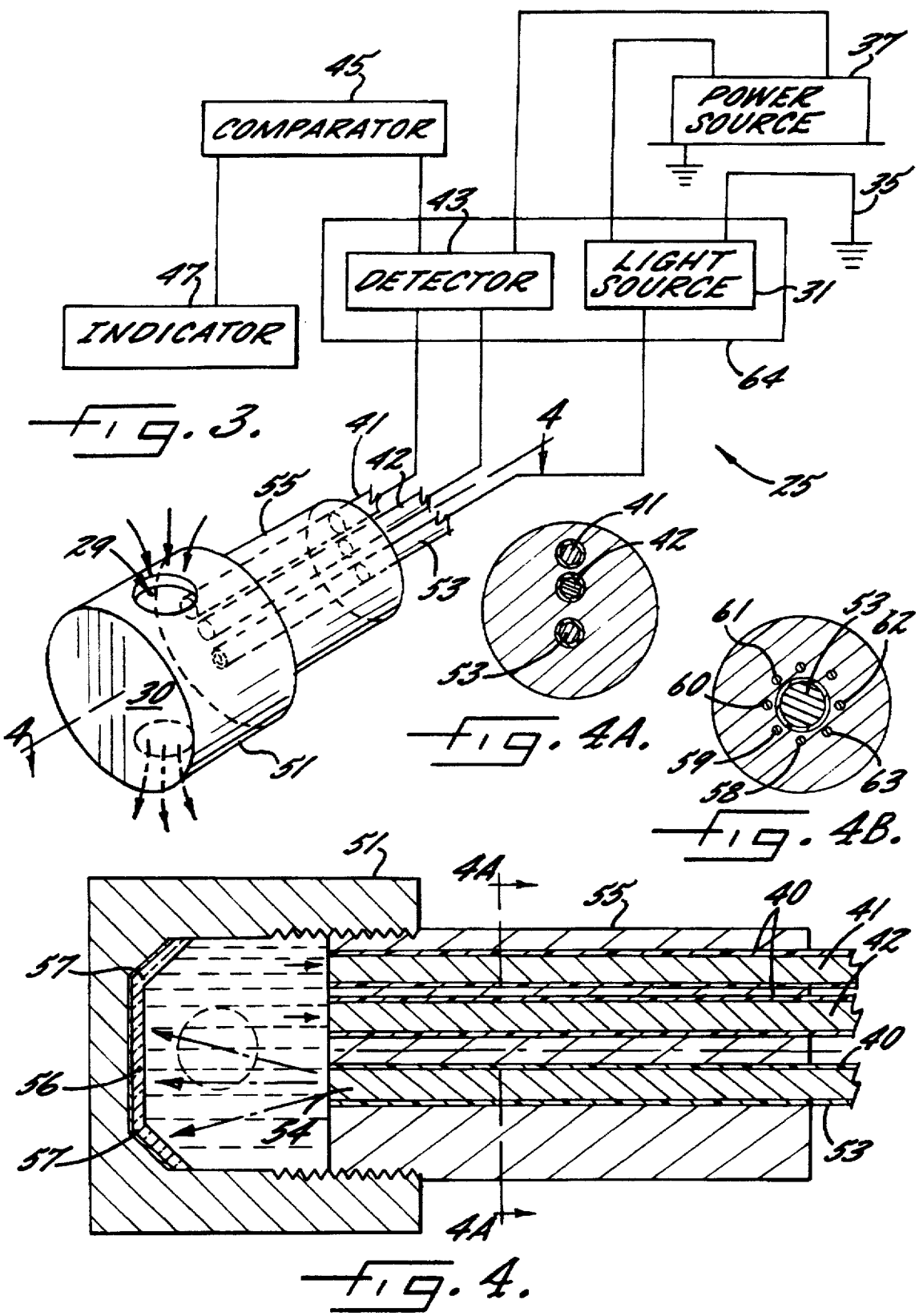

ETHYLENE GLYCOL

APPARATUS AND METHOD FOR DETERMINING THE CONCENTRATION OF SPECIES IN A SUBSTANCE

FIELD OF THE INVENTION

This invention relates to apparatus and methods for spectral analysis of various substances.

BACKGROUND OF THE INVENTION

One problem encountered in the use of lubricating oils, hydraulic fluid, brake fluid, and the like is determining when to renew the fluid. Crankcase oil in an automobile engine typically is changed based on mileage or time, taking into account driving conditions. Brake fluid, antifreeze, and transmission fluid normally are changed at regular intervals. However, time and mileage methods do not provide a precise indication of the degree of degradation of the oil or other fluid or contamination by wear particles, dust, water, or other species.

Methods based on time or mileage do not take into account the actual quality of the fluid that is being replaced, with the result that precious resources may not be fully utilized or may be used well beyond the full extent of their useful life in a contaminated or broken down condition. The consequences can range from increased expense associated with excessive fluid changes or premature engine wear to catastrophic failure. Dirty hydraulic fluid has been implicated in major airline disasters that have resulted in loss of life and extensive property damage.

Various attempts have been made to develop methods and apparatus for analyzing the quality of fluids such as motor oil. Methods of monitoring motor oil range from electrochemical analysis for hydrolysis products to mass spectroscopy for hydrocarbon structure. Some electro-optical devices have been proposed. For example, Wohlstein et al. U.S. Pat. No. 5,296,843 is directed toward comparing the difference in transmission of two wave lengths of light through crankcase oil to a preselected difference for clean oil to develop a signal when the oil is dirty.

Light signals of varying optical amplitude are converted into proportional electric signals of varying electrical amplitude. A voltage based on the ratio of the electrical outputs corresponding to the two wave lengths of light is produced through the use of converters and an analog divider and is compared to a predetermined voltage. A signaling means is activated when the measured voltage differs from the predetermined voltage by a preselected amount for alerting the user that the fluid has moved outside the range of acceptable operating parameters.

Yamada U.S. Pat. No. 5,076,397 describes an oil condition checking system for a marine propulsion unit. A detector is provided in the lower unit of an outboard motor for providing an automatic testing of the quantity and quality of the lubricant in the lower unit. The detector includes a light emitter and a light receiver that face each other and are disposed so that the lubricant will pass by them. The system includes an oil condition deciding circuit, which is a central processing unit programmed to compare the quality of the light transmitted with a predetermined value which is indicative of a satisfactory lubricant condition.

Kamiya et al. U.S. Pat. No. 4,699,509 describes a device for measuring the contamination of a lubricant. A light-emitting diode is positioned in a sensor opposite a photo-diode and spaced from the photodiode by a predetermined gap. Lubricant is fed through the gap. The amount of contaminant in the lubricant is obtained by observing the intensity of the light reaching the photodiode from the light emitting diode.

Gager U.S. Pat. No. 4,570,069 describes an on-board oil quality monitor that includes a tube for continuously removing and re-circulating oil from an engine. The tube has a transparent portion located within an infrared generator. Infrared light transmitted through the oil is received by a detector that produces a signal indicating excessive oil contamination if the intensity of the infra-red light transmitted to the detector through the oil is below a certain threshold.

Hochstein U.S. Pat. No. 4,635,473 describes an oil monitor assembly that can be removably attached to an oil reservoir. Concentric spaced electrodes are separated at their ends by electrical insulation. Perforations in the outer electrode allow oil into the annular space between the inner and outer electrodes. Degradation of motor oil is determined by measuring the decrease in resistivity provided by the oil between the inner and outer electrodes.

Kauffman U.S. Pat. No. 5,071,527 describes a method and apparatus for analysis of oils, lubricants and fluids, such as cooking oils. The method can be performed on-line in a dip-stick type electrode system. A voltage analysis and conductance measurements are performed to determine the anti-oxidant levels in the oil and whether oxidized species exceed preset values.

Megerle U.S. Pat. No. 5,089,780 describes an electrochemical cell in which electrodes are mounted on a plug for an engine oil pan. Conductivity measurements of the oil are transferred to a conductivity measuring device. The conductivity measuring device, which is external to the engine, is connected to a warning light or other display that provides the operator with an indication of the oil conductivity or an indication when the oil conductivity drops below a specified value.

Despite the number of devices that have been proposed, most people continue to rely on time and mileage as the principle indicators of oil quality in their engines. The above devices generally have drawbacks and problems associated with them that limit their acceptance and use.

SUMMARY OF THE INVENTION

In accordance with the present invention, an instrument and method are provided for determining the concentration of at least one species in a substance. The instrument can be inserted into the crankcase of a working engine and is capable of providing a continuous accurate indication of the quality of the motor oil in the crankcase and warning of catastrophic inclusions of coolant or water. Various types of contaminants can be detected and identified. The invention can also be used to determine the quality of a number of other substances, such as hydraulic fluid, cooking oil, diesel fuel, and others on a discrete or continuous basis.

In one embodiment, the instrument comprises a light path cell for a single broad band light source that is capable of being inserted into a working fluid, a means for receiving light that is transmitted through the fluid and separating the optical signals that are transmitted through the fluid based on the wavelengths of the signals, the means providing a link to a means that receives the transmitted optical signals as separate signals of different wavelengths and creates proportional electrical signals, a means for calculating the quality of the substance based on the optical signals as converted to electrical signals, and a readout to indicate the condition of the substance.

In another embodiment there is provided an instrument comprising a housing that has a chamber for receiving at least a portion of the substance to be analyzed and for interconnecting the optical transmitting and receiving portions of the apparatus. A broad band white light source is associated with the housing. The light source is positioned in fixed illuminating contact with the chamber for illuminating the substance in the chamber. A plurality of optical fibers are associated with the housing and are positioned in fixed relation to the chamber. The optical fibers receive light that has been transmitted through the substance. The optical fibers are preselected to transmit selected different wavelengths or bandwidths of light over the broad band spectrum of white light.

A means is provided for discriminating among the optical signals transmitted by the optical fibers. This means is operatively connected to the optical fibers. A means is provided for generating from the separate optical signals electrical signals that are proportional to the absorbance of the optical signals by the substance being examined. Light signals of varying optical amplitude are converted into proportional electrical signals of varying electrical amplitude. For example, a peak in amplitude in the electrical signal corresponding to absorbance of an optical signal at 2000 to 2200 nm signals the presence of ethylene glycol in oil. More specifically, the discriminating means and the means for generating electrical signals proportional to the optical signals are included in a multiband segmented detector that is physically aligned with the individual optical fibers that separate the light transmitted through the substance.

A comparator is electrically connected to the detector means for generating electrical signals. The comparator includes means for receiving electrical signals of varying amplitude and means for determining the concentration of at least one species in the substance in dependence upon the absorbance of the optical signal as light is transmitted through the substance. More specifically, the comparator comprises an electronic circuit including a multiple channel amplifier for developing the electrical signal and a microprocessor for receiving the electrical signal, evaluating the signal, and determining the concentration of at least one species. The comparison can be based on voltage measurement, current measurement, or resistance.

In additional embodiments there is provided an indicator or display device operatively connected to the comparator for displaying to a user of the device an indication of the concentration of at least one species in the substance. More specifically, the display device is electrically connected to the comparator and includes multiple light emitting diodes for displaying the concentration of at least one species based on the electrical signal received from the comparator. Alternatively, a simple ohmmeter or galvanometer can be electrically connected to the detector means.

The instrument is capable of analysis of most any substance capable of transmitting light and including species that have some absorbance in a selected range of wavelengths. More typically, the substance will be a fluid selected from among motor oil, cooking oil, hydraulic fluid, diesel fuel, brake fluid, transmission fluid, antifreeze, gasoline, and light gaseous and liquid hydrocarbons. For example, motor oil, transmission fluid, hydraulic fluid, and brake fluid can be analyzed for the presence and concentration of diesel fuel, gasoline, water, ethylene glycol, wear particles, and antioxidants.

The invention also provides a method for determining the concentration of at least one species in a substance. In the practice of the method, a substance is illuminated with broad band light from a single source. The light that is transmitted through the substance from the broad band light source is segregated into optical signals that have distinct wavelengths. The transmitted light is segregated into optical signals having distinct wavelengths by using various optical fibers preselected to transmit the specific wavelength for which each fiber is selected. These optical signals are converted into electrical signals of varying amplitude that are proportional to the optical signals and reflect absorbance of the optical signals as the light is transmitted through the substance. The concentration of at least one species in the substance is determined based on the electrical signals.

In additional embodiments, the method also includes the step of displaying to a user of the instrument an indication of the concentration of at least one species in a substance. Typically, the substance that is analyzed is a fluid and the step of illuminating the substance with a broad band light source comprises flowing the fluid through a chamber and illuminating the fluid in the chamber with a white light source.

In more specific embodiments, the step of converting the optical signals into electrical signals includes the step of discriminating among the optical signals. The electrical signals are amplified and these amplified signals are evaluated to determine the concentration of at least one species. To evaluate the signals, a plot of wavelength versus absorbance is prepared and the area under the resulting curve is integrated from one wavelength to the next. The resulting data is compared to similarly obtained data for a pure substance to evaluate the condition of the substance and the presence and concentration of species in the substance.

The light source can be placed outside the engine and a fiber optic link capable of transmitting the broad band light source can be used to transmit the light from the source to the substance to be analyzed. Alternatively, the light source can be fixed to the housing for illumination of the substance flowing through the housing. The light source, housing, and optical fibers can all be selected to sustain harsh environments as may be encountered in the crankcase of an automobile, truck, or marine engine. A light source, such as an inexpensive tungsten filament incandescent lamp, can be selected for this purpose.

Thus, the invention provides an instrument and method capable of analyzing the quality of motor oil in situ in the environment in which it is in use and while it is being used. The instrument and method are capable of providing a discrete or a continuous indication of the degree of contamination or breakdown condition of the fluid. A real time plot of the condition of the oil or other fluid can be obtained and used to observe the condition of the oil or other fluid over time. Fluid renewals can be scheduled with greater efficiency and at reduced cost as compared to prior methods.

BRIEF DESCRIPTION OF THE DRAWINGS

Some of the features and advantages of the invention have been stated. Other advantages will become apparent as the description of the invention proceeds, taking in conjunction with the accompanying drawings, in which:

FIG. 3 represents a perspective view of an alternative preferred embodiment of the apparatus of the present invention and includes a schematic diagram of the electronic components of the apparatus;

FIG. 4 represents a longitudinal section through a portion of the apparatus that has been taken along line 4—4 of FIG. 3;

FIG. 4A represents a transverse section through a portion of the apparatus that has been taken along line 4A—4A of FIG. 4;

FIG. 4B represents an alternative configuration for the subject matter of FIG. 4A;

DESCRIPTION OF THE PREFERRED EMBODIMENTS

The invention will now be described more fully with reference to the accompanying drawings, which illustrate particular embodiments of the apparatus. In the preferred embodiments, the invention includes an instrument that can be placed in direct contact with motor oil or similar substances in the environment in which they are being used for in situ determination of the concentration of at least one species in the substance. Optical fibers can be used to convey optical signals to electronic components that are maintained outside the environment in which the fluid is being used.

Figure 1:
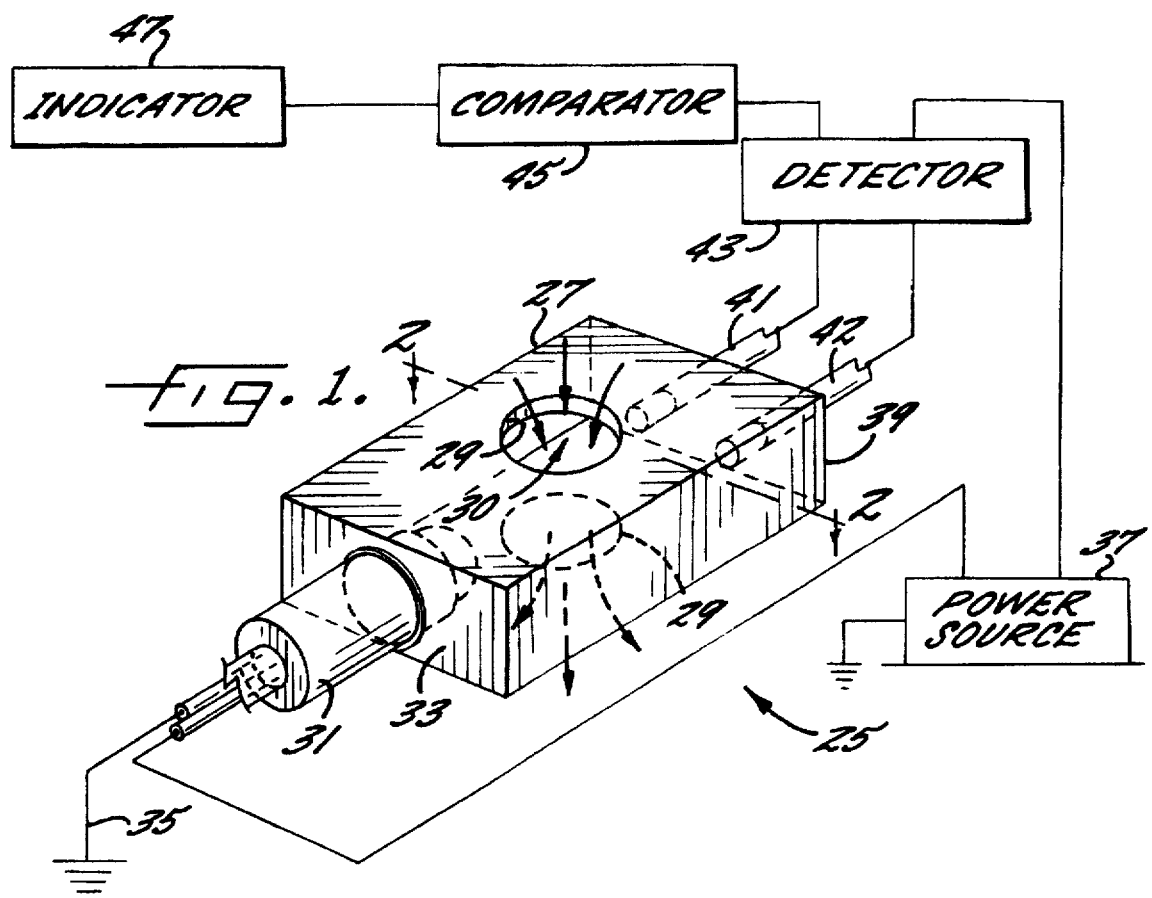
FIG. 1 represents a perspective view of a preferred embodiment of the apparatus of the invention and includes a schematic diagram of the electronic components of the apparatus.

An apparatus is generally identified in FIG. 1 by the numeral 25. FIG. 1 represents, for example, an oil quality monitor that could be placed in the motor oil of an engine through the dipstick tube or that could be configured as a replacement for the drain plug. The apparatus of FIG. 1 includes a flow-through housing 27 having an aperture 29 on each of two sides thereof defining a passage for the flow of fluid, such as motor oil, into and out of a chamber 30 that is defined by the interior of the housing. Flow of fluid through the housing is indicated by the directional arrows in FIG. 1.

Flow-through housing 27 should be constructed of components that are appropriate for the environment in which the device is being used. Stainless steel and other metals, and TEFLON materials are appropriate for use in an automobile crankcase, for example.

Figure 2:
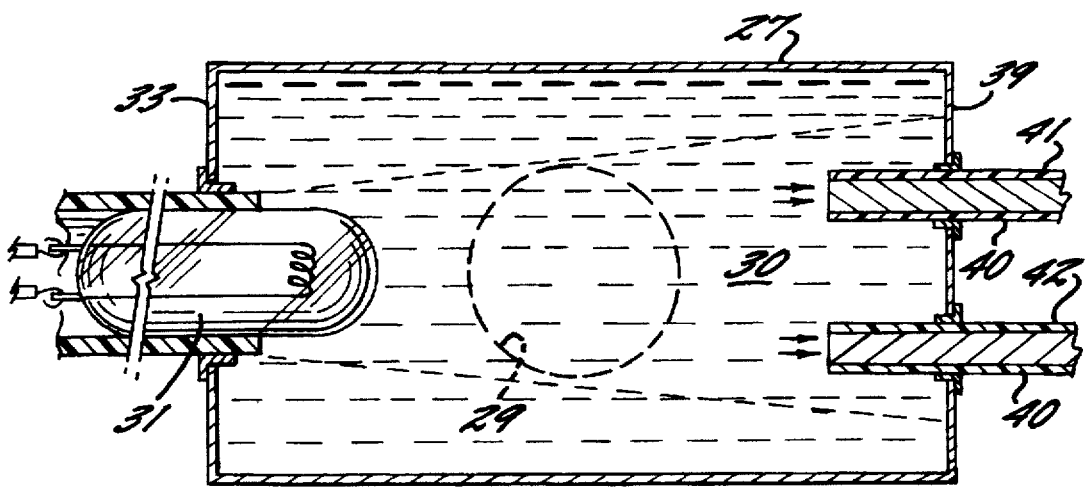
FIG. 2 represents a longitudinal section through a portion of the apparatus that has been taken along line 2—2 of FIG. 1.

Associated with the flow-through housing is a broad band white light source 31. In FIGS. 1 and 2, the broad band white light source is shown fixed to one end 33 of the housing and held in fixed illuminating contact with the interior of the housing for illumination of the oil or other substance in the chamber. The light source is immersed in the oil that is in the interior of the flow-through housing in the embodiment of FIGS. 1 and 2.

The light source 31 can be energized in a variety of manners such as by being connected between ground 35 and power source 37, which can be a 12 Volt automobile battery, as shown in FIG. 1. One suitable light source is an inexpensive tungsten filament incandescent lamp. Halogen, quartz, or krypton lamps should also be useful and should withstand the environment.

At the opposite end 39 of the flow-through housing 27, at least two optical fibers 41 and 42 in jackets 40 are associated with the housing in fixed relation to the flow-through chamber for receiving light that has been transmitted from the light source through the substance in the flow-through chamber. The optical fibers are preselected to transmit light of different wavelengths or bandwidths, to attenuate light outside the bandwidth transmitted, and to withstand the environment.

The optical fibers transmit various optical signals to a detector 43 that provides a means that is operatively connected to the optical fibers for discriminating among the optical signals transmitted by the optical fibers. The detector 43 preferably is a multiband segmented detector that is physically aligned with the individual fibers of the fiber optic bundle. The multiband segmented detector receives the optical signals, discriminates among the signals, and includes means for generating electrical signals that are proportional to the absolute strength or intensity of the optical signals. The detector analyzes the absolute strength or intensity of the light received from the optical fibers and then converts the light signals of varying optical amplitude into proportional electrical signals of varying electrical amplitude. The detector can receive power input from the same source as the light source. The light source and detector can be energized using separate voltage or current as required.

The outputs from the detector, which are the electrical signals that are proportional to the optical signals that the detector received, is transmitted to a comparator 45 that is electrically connected to the detector. The comparator includes means for receiving the electrical signals from the detector and means for determining the concentration of at least one species in the substance in dependence upon the absorbance of the optical signal as light is transmitted through the substance. If the analysis of the electrical signals is based on voltage or current, then the comparator can comprise a simple resistor. The comparator may comprise an electronic circuit that includes a multiple channel amplifier and an associated microprocessor. Alternatively, the amplifier can be associated with the detector. The amplifier scales or amplifies the electrical signals to levels that the microprocessor is adapted to receive. The microprocessor receives the electrical signals, evaluates the signals, and determines the concentration of at least one species. A Reduced Instruction Set Chip has been determined to be a useful microprocessor in performing many of the electronic functions.

The instrument further comprises an indicator or display device, shown in FIG. 1 as indicator 47, that is operatively connected to the comparator for displaying to a user an indication of the concentration of at least one species in the substance. An electrical signal from the comparator 45 corresponding to the concentration of the species in the substance is transmitted to the indicator 47 for display. The indicator can be, for example, a multiple light emitting diode display for displaying the concentration of at least one species based on the electrical signal received from the comparator.

The indicator reading can be based on voltage, current, or resistance for each of the electrical signals from the detector. For reading a resistance, or impedance, a power source is not required for the detector. A resistance reading from an ohmmeter has its own voltage source. The indicator can read in-line with the comparator/resistor as a voltage sensitive device with the indicator to ground or across the resistor with the resistor to ground as a current sensitive device.

Turning now to FIG. 2. FIG. 2 illustrates a longitudinal section taken along line 2—2 of FIG. 1. Light emitted from the tungsten filament incandescent lamp 31 is shown transmitted through the housing 27 and entering motor oil in the flow-through chamber 30. The transmitted light is received by optical fibers 41 and 42, each of which transmits the specific wavelength or bandwidth for light for which it has been preselected.

An alternative embodiment is shown in FIG. 3 in which the light source 31 is remote from the flow-through chamber 30 so as not to be immersed in the oil, but remains in fixed illuminating contact with the flow-through chamber. Similar elements or parts of the apparatus illustrated in FIGS. 3 and 4 are numbered similarly to the parts of FIGS. 1 and 2. The embodiment of FIGS. 3 and 4 includes an optical fiber 53 capable of transmitting broad band white light from the light source to a reflective flow-through housing 51.

FIG. 4 is analogous to FIG. 2. FIG. 4 illustrates a longitudinal section taken along line 4—4 of the device of FIG. 3. FIG. 4 illustrates the reflective housing 51, transmission of light through the flow-through chamber 30, and reflection back to the optical fibers 41 and 42 for receipt and transmission of optical signals.

As illustrated in FIGS. 3 and 4, the optical fiber 53 is held in fixed illuminating contact with the flow-through chamber 30 by insertion through a channel defined by a threaded cylindrical member 55 that is threadedly engaged with the flow-through housing 51. A pair of optical fibers 41 and 42 are contained in the threaded cylindrical member parallel to the broad band optical fiber 53. FIG. 4A shows the orientation of the optical fibers 41, 42, and 53 in the threaded cylindrical member 55. Optical fibers 41 and 42 are preselected for transmitting different selected bandwidths of light from the light reflected back from fiber 53.

A reflective surface 56 is contained within the flow-through housing 51 opposite the terminae of the optical fibers 41, 42, and 53 to reflect light transmitted from the broad band optical fiber 53. A reflective surface that includes one or more corner reflectors 57 has been found to be particularly useful. The receiving fibers 41 and 42 are not in the direct line-of-sight of the reflected light. The reflective surface should be made of metal or high temperature plastics suitable for the environment.

Light transmitted by the broad band optical fiber 53 enters the oil in the flow-through chamber and is reflected off the reflective surface 57 back to the threaded cylindrical member. The reflected light is received by the optical fibers 41 and 42 and transmitted to a detector 43 as described with respect to FIG. 1. A comparator 45, display 47, and power source 37, which is a 12 Volt battery, are also included as described with respect to FIG. 1.

The optical fibers act as a filter to separate the optical signals that are transmitted through the substance in the chamber based upon the wavelengths of the optical signals. For example, one optical fiber may transmit optical signals in the range of from about 380 nm to 800 nm and another fiber may transmit light in the range of from 2000 to 2200 nm, while attenuating light transmission outside these bandwidths. A fiber that transmits optical signals having a wavelength of from 2000 to 2200 nm is generally desirable in the analysis of motor oil since ethylene glycol absorbs light at this wavelength. Such a fiber could signal the presence of ethylene glycol in the oil whether or not the oil is otherwise clean. Appropriate wavelengths for analysis of various substances and the selection of the optical fibers to separate optical signals for conversion to electrical signals and analysis typically will need to be determined empirically.

Silicon rubber fiber optic materials that have been developed at Oak Ridge National Laboratory pass light from 550 to 700 nm and attenuate light outside this bandwidth. Silicon rubber fiber optic materials are also suitable for the high temperature applications that could be encountered in an operating combustion engine. Operating temperatures can be expected to reach or exceed 300° F. Other suitable materials include doped glass fibers or doped fluoroethylene polymer (TEFLON) fibers. There are a wide range of dopants commercially available for the manufacture of optical fibers for use in the invention, including metal salt crystals, colored dyes, and the compounds used in laser rods for obtaining a specific frequency of light.

A plurality of optical fibers for transmitting various bandwidths within the broad spectrum of white light can be used for additional separation of the optical signal transmitted through the substance in the chamber in the housing, depending upon need. A variety of fibers that transmit different bandwidths can be preselected and assembled into a bundle. Alternatively, a bundle of optical fibers of varying light transmissive properties can be drawn.

An alternative configuration for the broad band transmitting fiber and the fibers for transmitting different, selected bandwidths is illustrated in FIG. 4B as a transverse section through the cylindrical member 55. The fibers could be drawn as a single fiber unit with the broad band transmitting fiber 53 in, for example, the center, and the several different fibers 58, 59, 60, 61, 62, and 63 for transmitting selected bandwidths surrounding the center fiber. The broad band light transmitted by the centrally located broad band optical fiber 53 would then be reflected back to the selected bandwidth fibers in accordance with the specific absorbance of the individual species concentration in the oil. The detector would be a quadrant or other common sector device with each sector receiving only the light of a particular bandwidth. For example, the optical fibers could be selected to transmit, separately, light at 450, 500, 600, and 650 nm.

The light source and detector can be contained within a single package 64 as shown in FIG. 3. This light source and detector package could be substituted with a separate package that contains a different type of instrument or detector for discriminating among the optical signals that are received through the fiber optic bundle. For example, a grating, prism, or etalon could be used for receiving the transmitted light and discriminating among the signals by separating the light based upon the wavelengths of the optical signals. These devices could eliminate the need for a fiber optic bundle to filter the various signals prior to discrimination. A single broad band optical fiber could be used to transmit the optical signals of each of the different wavelengths from the flow-through chamber 30. However, in some instances these alternatives would require moving parts such as a piezoelectric or shape memory metal translator.

Figure 5:
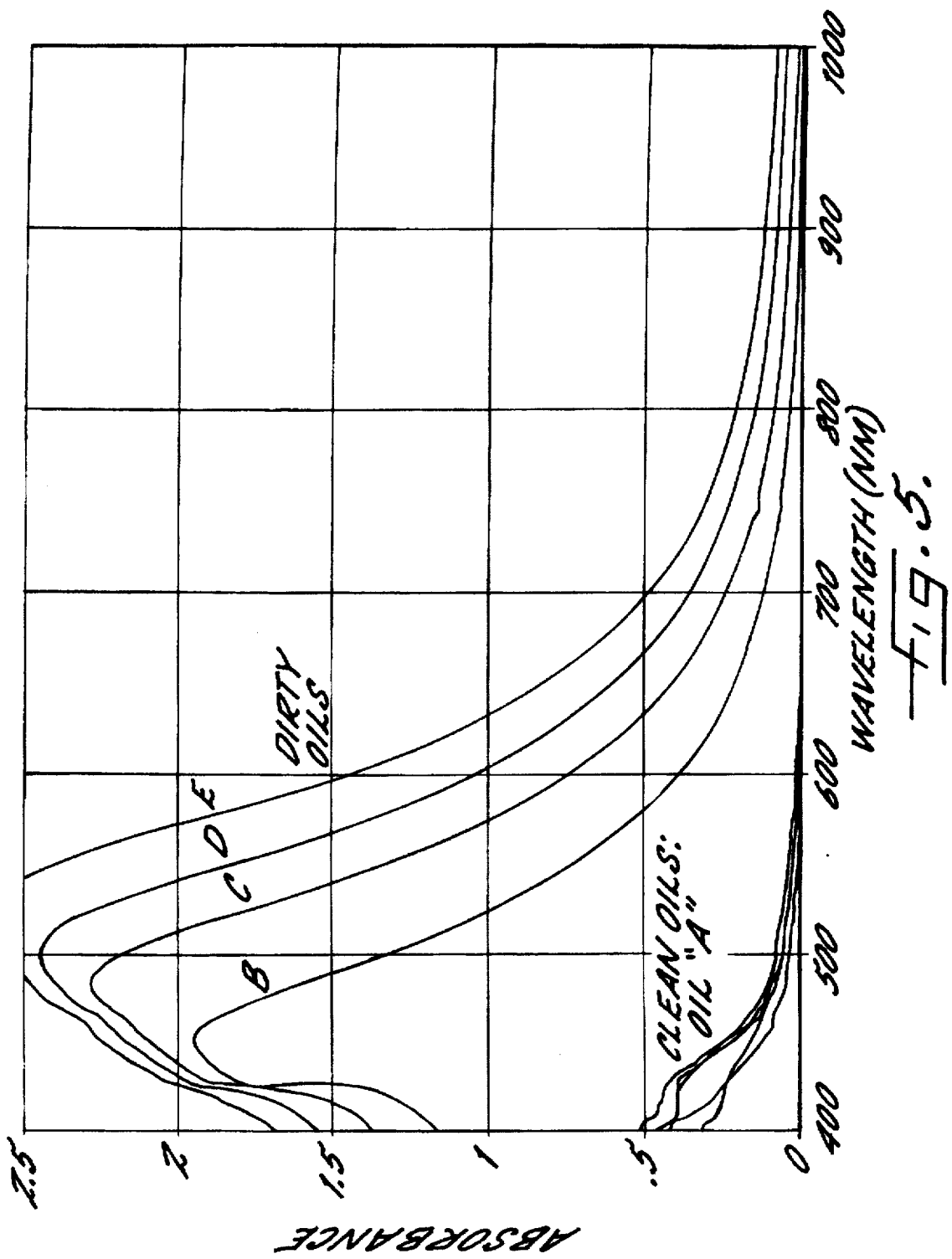
FIG. 5 represents a plot of absorbance versus wavelength for various conditions of contamination of motor oil.

Turning now to FIG. 5, FIG. 5 illustrates the application of the method of the invention using apparatus as represented in FIGS. 1 through 4 and as described above. The plot is based upon the following data as shown below in Table I. The data illustrated in FIG. 5 and shown in Table I below are based on a clean motor oil that was mixed with various proportions of dirty oil obtained from a local mechanic. Oil A is basically a clean oil. Oil B is 75% clean oil and 25% dirty oil. Oil C is 50% clean oil and 50% dirty oil. Dirty Oil D is clean oil mixed with 75% of the dirty oil obtained from the local mechanic. The dirty oil obtained from the local mechanic is Dirty Oil E and is described on a relative basis as 100% contaminated. The data collected show an absorbance in the range of 400 to 700 nm as was previously described by Wohlstein in U.S. Pat. No. 5,296,843. However, Wohlstein selected the wavelengths that include 450 and 550 nm for analysis, which excludes a sensitive determination of the intrusion of fuel and ethylene glycol, or other antifreeze. Additionally, the ratio of absorbance values at 450 nm and at 550 nm approaches unity as the oil becomes more contaminated. The Wohlstein method takes measurements on each side of the peak value for absorbance. The maximum peak value drifts towards longer wavelength. Thus, the Wohlstein method shows lower sensitivity to change at 450 nm than at 550 nm as can be seen from the data in Table I.

TABLE I

DIRECT WAVELENGTH READINGS OF DIRTY OIL

| OILS | WAVELENGTH | | | | |
|---|---|---|---|---|---|
| | 450 | 500 | 550 | 600 | 700 |
| A | 0.25 | 0.10 | 0.05 | 0.00 | 0.00 |
| B | 1.90 | 1.30 | 0.70 | 0.35 | 0.125 |
| C | 2.15 | 2.20 | 1.30 | 0.75 | 0.25 |
| D | 2.20 | 2.40 | 1.85 | 1.05 | 0.375 |
| E | 2.25 | 2.70 | 2.35 | 1.45 | 0.50 |

Table II, below, shows the poor sensitivity of methods that are based on data taken from each side of the peak absorbance. Analysis based on such a method could lead to a situation where the readings obtained increase toward a dirty reading for the oil, but as the oil becomes more contaminated the reading then approaches that for clean oil.

However, peak height detection from a broader bandwidth single source, as described in the invention herein, does not show double values for contamination versus absorbance and provides a continuous increase in absorbance versus contamination for any single wavelength from about 380 to about 800 nm independent of peak wavelength value.

TABLE II

METHOD OF WOHLSTEIN ET AL.
U.S. PAT. NO. 5,296,843

RATIO OF LOGS OF AT WAVELENGTHS INDICATED

| OILS | 450/550 | LOG | 500/600 | LOG | 600/700 | LOG |
|---|---|---|---|---|---|---|
| A | 2.00 | 0.301 | INDT | INDT | INDT | INDT |
| B | 2.60 | 0.415 | 3.70 | 0.568 | 2.80 | 0.447 |
| C | 1.75 | 0.243 | 2.93 | 0.467 | 3.00 | 0.477 |

TABLE II-continued

METHOD OF WOHLSTEIN ET AL.
U.S. PAT. NO. 5,296,843

RATIO OF LOGS OF AT WAVELENGTHS INDICATED

| OILS | 450/550 | LOG | 500/600 | LOG | 600/700 | LOG |
|---|---|---|---|---|---|---|
| D | 1.25 | 0.097 | 2.29 | 0.360 | 2.80 | 0.447 |
| E | 1.00 | 0.00 | 1.86 | 0.270 | 2.90 | 0.462 |

Figure 12:
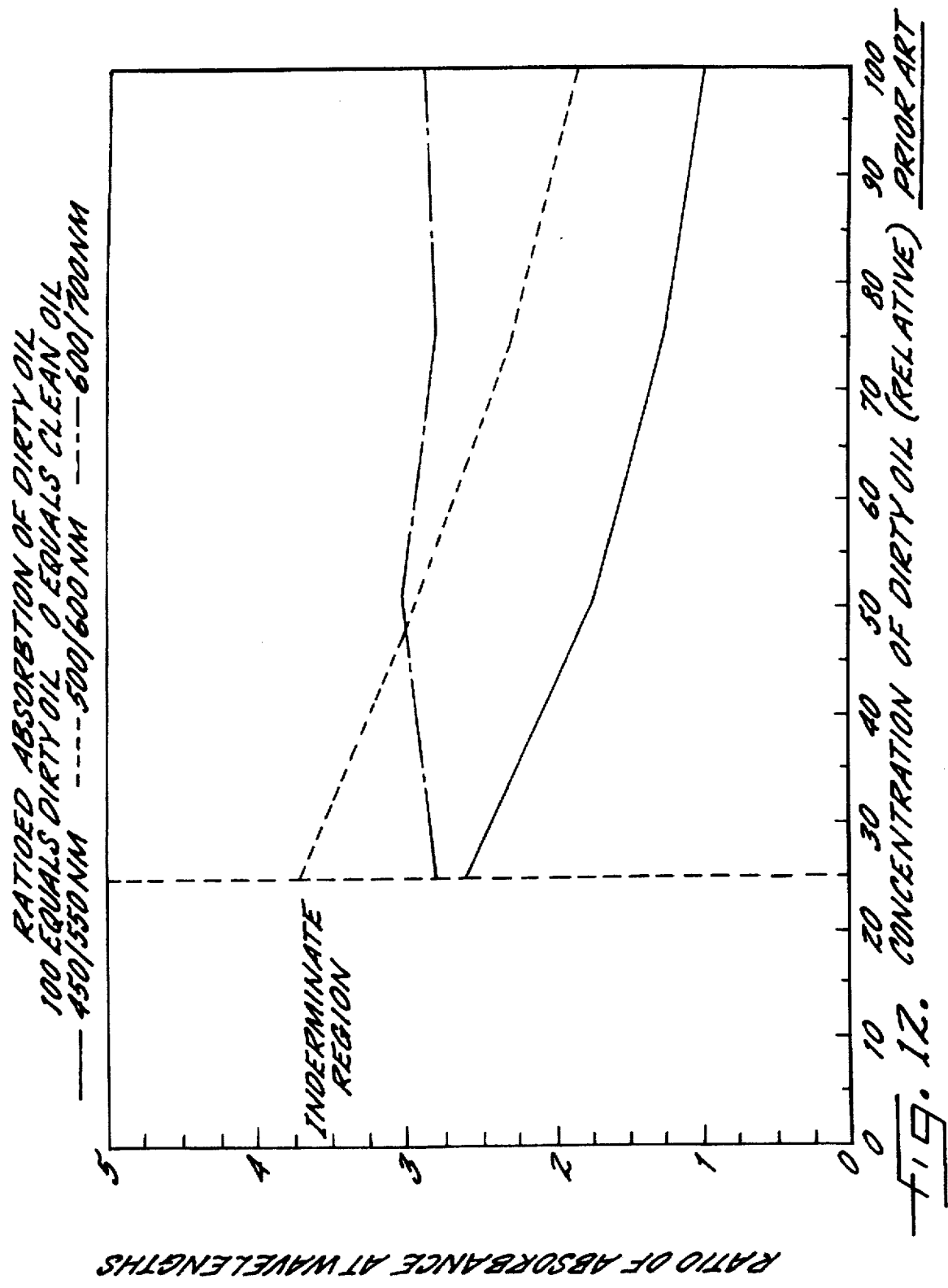
FIG. 12 is a representation of one method of determining the concentration of dirty oil based on the prior art in which a ratio is taken of absorbance at two different wavelengths and is plotted against concentration.
Figure 13:
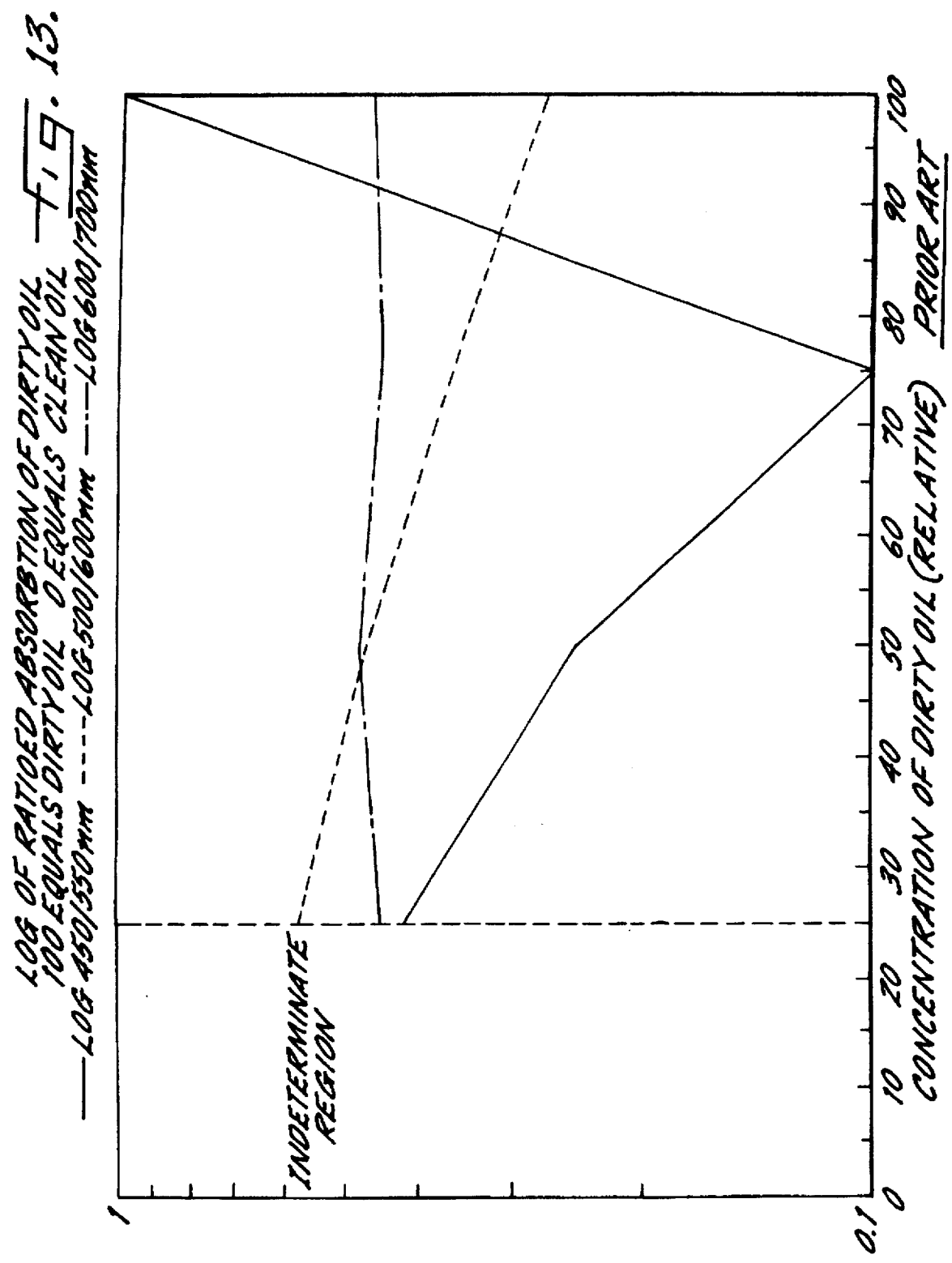
FIG. 13 is similar to FIG. 12, but plots a log ratio against concentration of dirty oil similar to the method of Wohlstein et al. U.S. Pat. No. 5,296,843.

The data in Table II is illustrated graphically in FIGS. 12 and 13. If the ratio of readings at 450 and 550 nm are taken at two points where the slope is in the same direction then the ratio may lead to double values. These figures and the data in Table II show clearly that, in the case of the method of Wohlstein, the ratios provide identical readings for dirty oil at different concentrations. If the first of the data is from a point on the spectra where the absorbance is increasing and the second is from a point on the spectra where the absorbance is decreasing, then, at some point, two concentration values are obtained for a given absorbency. In contrast, in the method of the invention described herein, the concentration of a species in a substance is measured by optical absorbance from a single bandpass reading. The area under the peak from one wavelength to the second is integrated and the concentration is accurately determined. The peak will usually increase in bandwidth as well as amplitude as the oil becomes contaminated, and so optical measurement of the entire bandwidth is preferred. However, such measurements, based upon the entire spectrum, typically have required expensive scanning or multi-element spectrometer devices.

Figure 6:
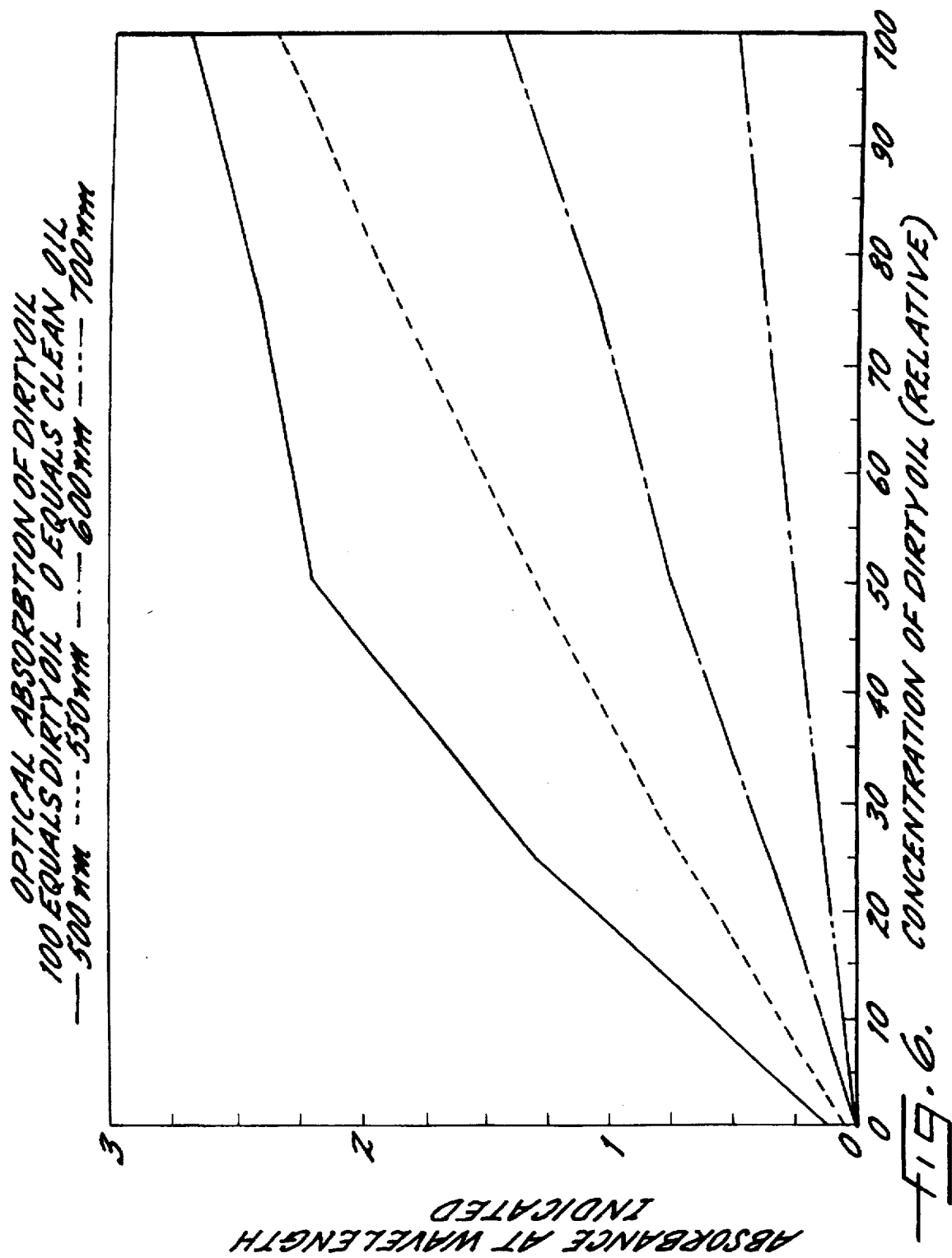
FIG. 6 represents a plot of the concentration of dirty motor oil against absorbance at four different wavelengths.

FIG. 6 illustrates graphically a continuous increase in absorbance at the indicated wavelengths when plotted against concentration of dirty oil. Absorbance is plotted at 500 nm, 550 nm, 600 nm, and 700 nm. Clearly, the increase in contamination of dirty oil can be followed continuously from a clean state to a contaminated state without double values of absorbance at any particular concentration.

Figure 7:
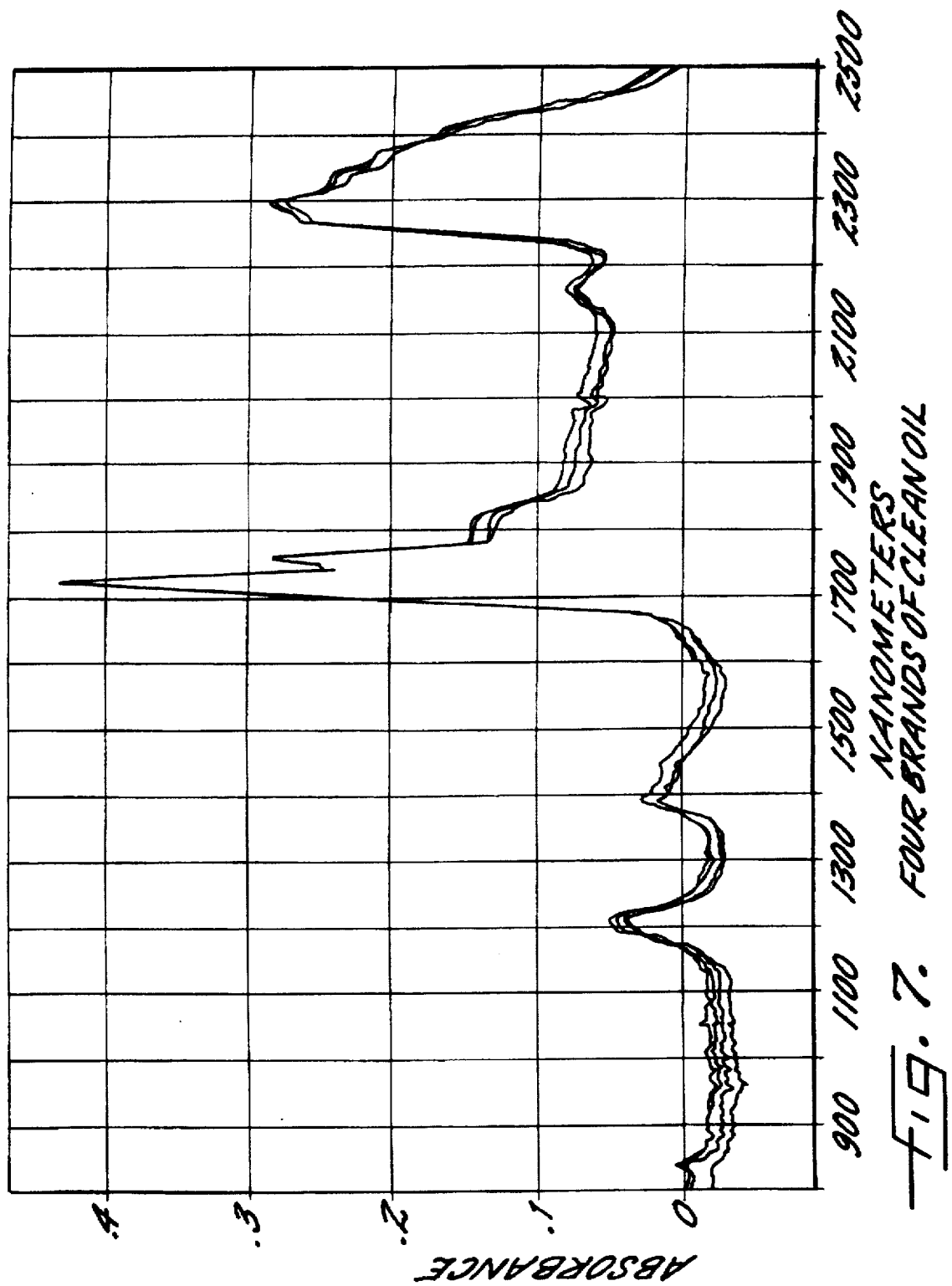
FIG. 7 represents a plot of absorbance versus wavelength for four different brands of clean motor oil at wavelengths of from about 900 to 2500 nm.

FIG. 7 shows absorbance for four different brands of clean oil at wavelengths of from about 800 to 2500 nm. These oils included Shell Fire and Ice, Havoline, Exxon SuperFlo, and STP 500.

Figure 8:
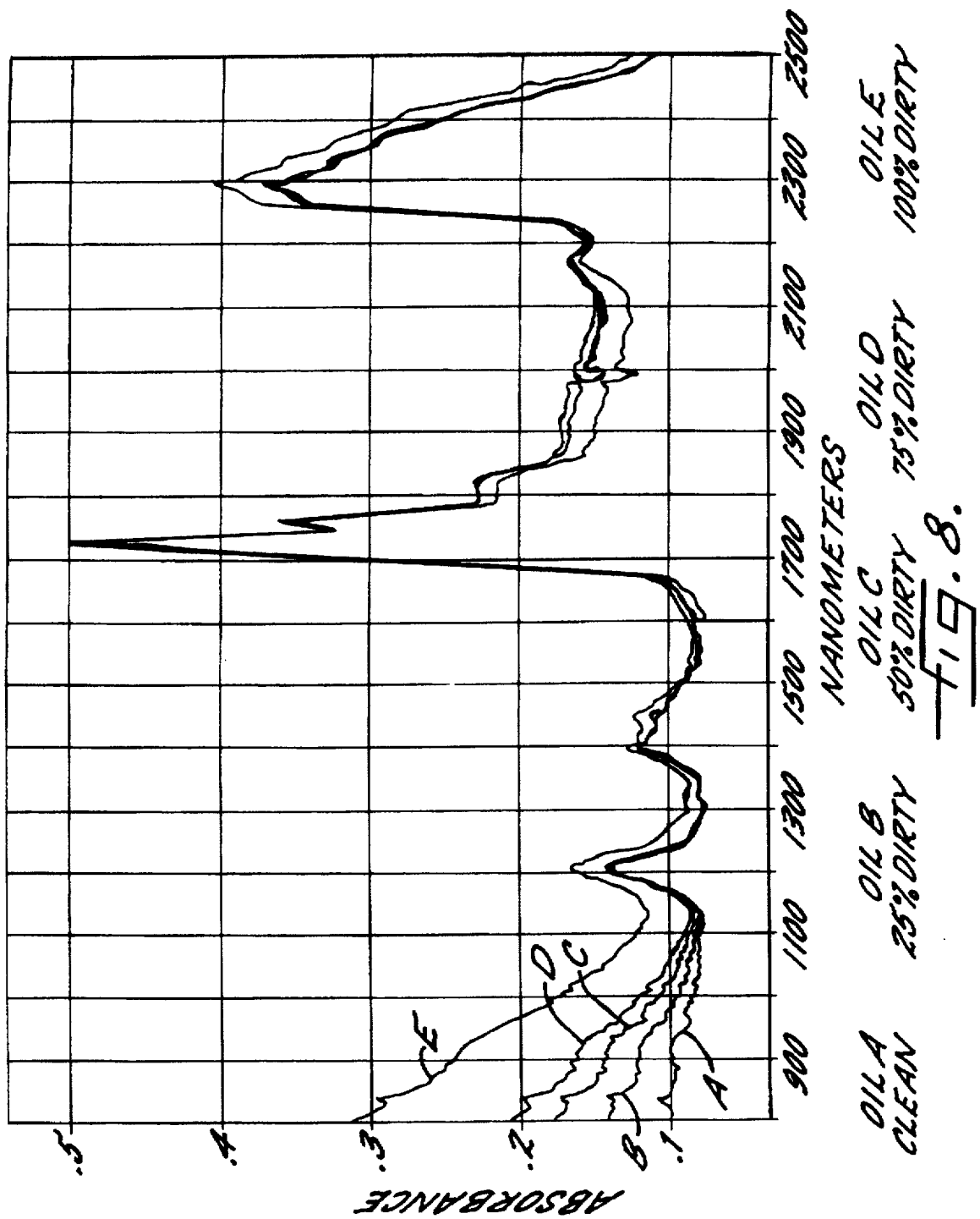
FIG. 8 represents a plot of absorbance versus wavelength for five motor oils in varying degrees of contamination at from about 900 to 2500 nm.
Figure 9:
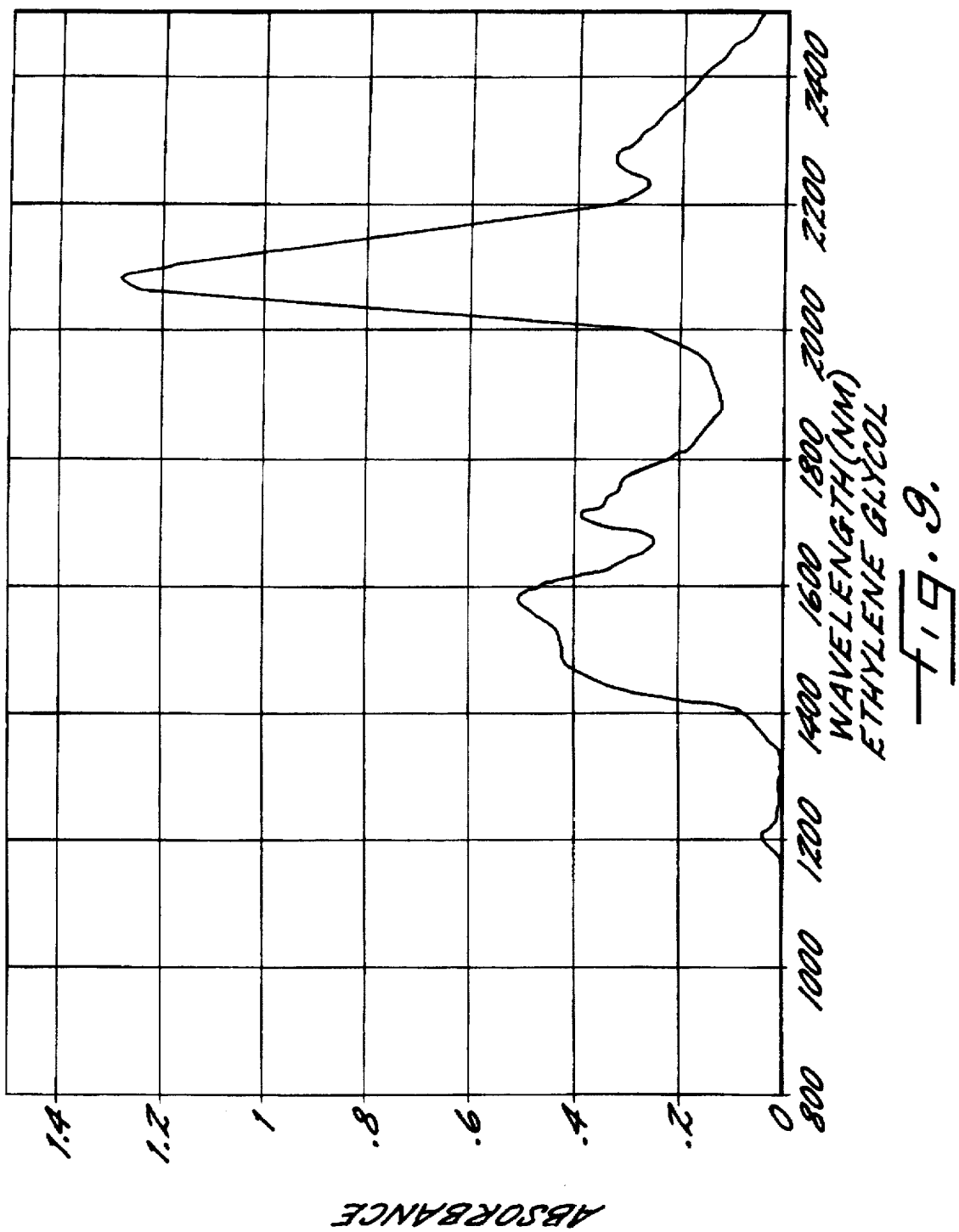
FIG. 9 represents a plot of absorbance versus wavelength for ethylene glycol antifreeze at from about 800 to 2400 nm.

FIG. 8 illustrates graphically absorbance for the oils A, B, C, D and E, in relative stages of contamination, that are the same oils as those used in FIG. 5. Very little difference in absorbance is shown between the dirtiest oil E and the cleanest oil A from about 1100 to 2500 nm. Clearly, when compared to FIG. 5 and the graphical representation of absorbance at 400 nm to 1000 nm, the best data for spectral analysis of motor oil comes in the range of from about 400 to 700 nm. As shown in FIG. 6, the best data for motor oil is developed at about 550 nm.

However, a broad band white light source that includes wavelengths up to 2500 nm is useful. A single optical fiber that attenuates wavelengths outside the range of from 2000 to 2200 and passes wavelengths in the range of from 2000 to 2200 could provide an accurate indication of the concentration of ethylene glycol if any, in oil, which is the principle constituent of antifreeze. Thus, catastrophic inclusions of ethylene glycol, and small ethylene glycol leaks into the oil pan could be detected, hopefully prior to costly damage to the engine.

Figure 10:
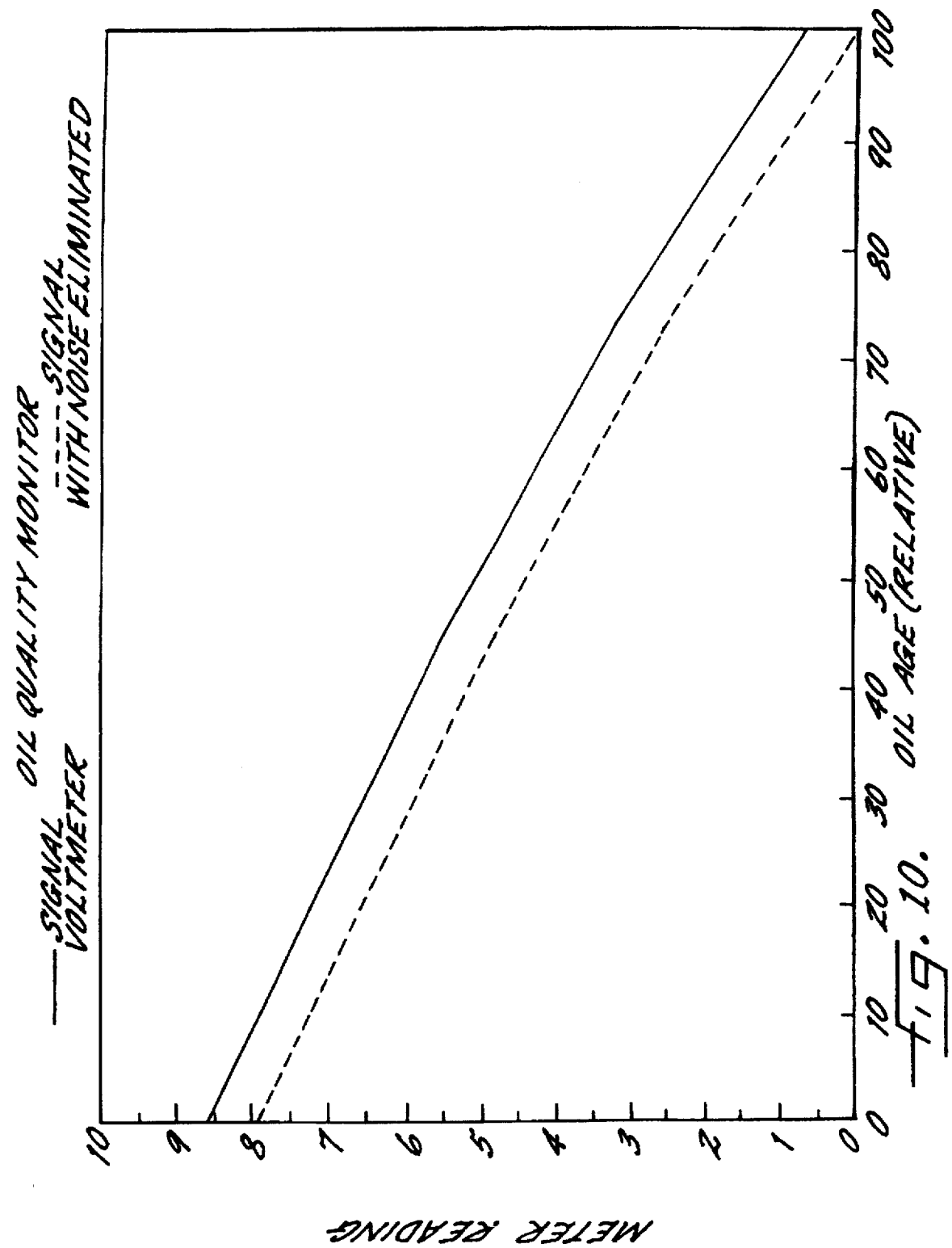
FIGS. 10 and 11 represent plots of time against various meter readouts for motor oil from the apparatus and method of the invention and reflect the quality of the oil over time.
Figure 11:
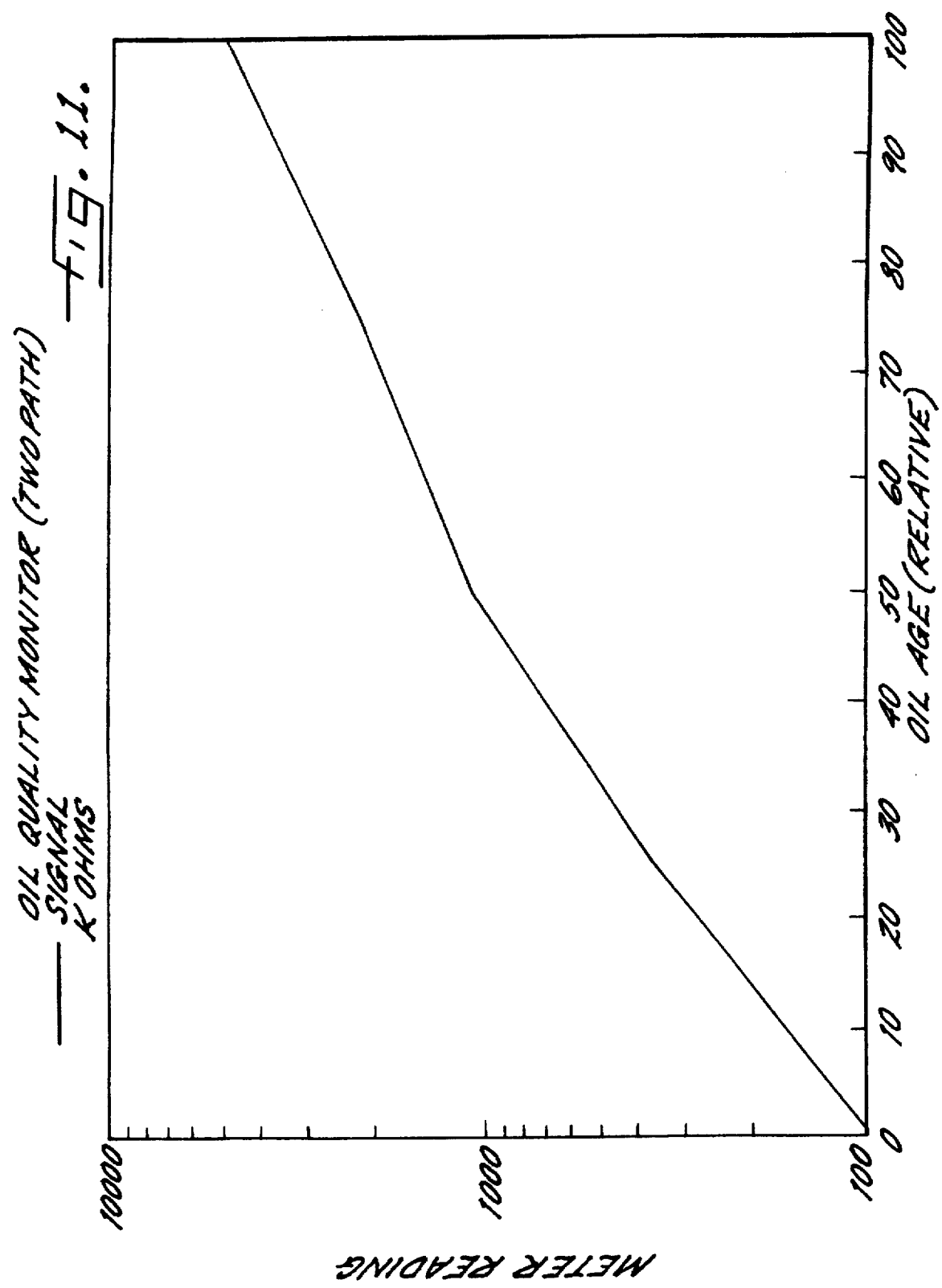

FIGS. 10 and 11 illustrate degradation of motor oil over time as a plot of relative oil age against a meter reading. The meter reading in FIG. 10 is from a low cost and simple galvanometer. The meter reading in FIG. 11 is from an ohmmeter. The output from the comparator is sent to the meter or bar graph display to show in real time the degradation of the oil.

The device described above and illustrated in FIGS. 1 through 4 is particularly inexpensive. Additional functionalities can be added at higher costs. For example, Professor Francis Yu of Pennsylvania State University has recently described spacial speckle multimode fiber sensors, which have been called fiber speckle gram sensors, or FSS, that could be used in combination with the measurement of absorbance of light by the oil to give increased information about metallic particles contained in the oil. See *Applied Optics*, Vol. 33, No. 22, Aug. 1, 1994 at pages 5202 through 5203. In addition to spectral analysis, temporal, spatial, polarization, and temperature analyses can all be performed in a working engine or other fluid reservoir without withdrawing the fluid from reservoir. Spectral analysis can be performed over time to provide a time-dependent indication of oil degradation. Oil level could be determined depending on the depth of placement of the device in the oil source. Spatial data can be used to indicate particle content. If warranted by expense, polarization methods should be considered. Decomposition of antioxidants can be determined.

Figure 14:
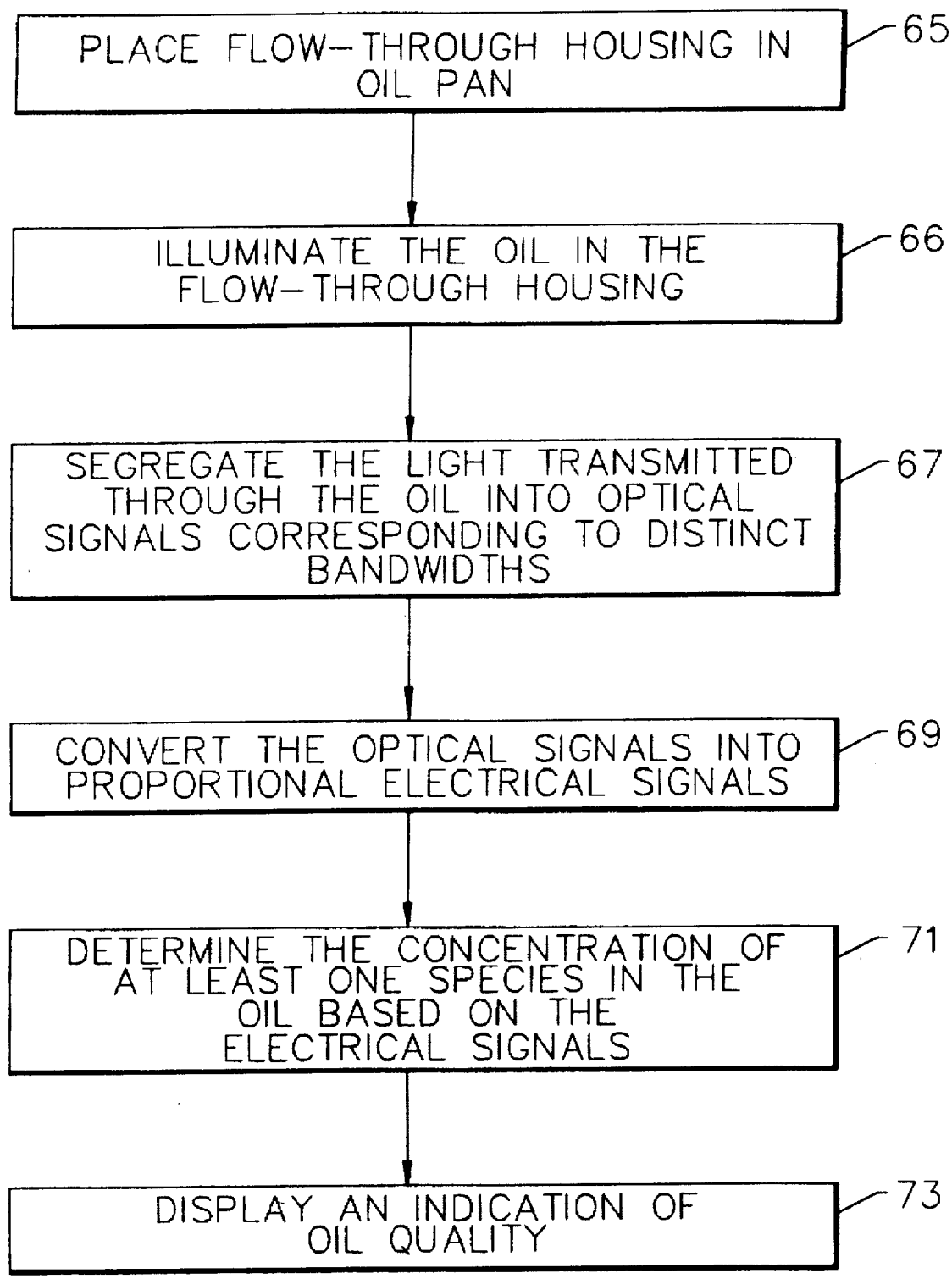
FIG. 14 is a flow diagram depicting the steps performed in the practice of the invention.

Turning now to FIG. 14, FIG. 14 is a flow diagram showing generally the steps taken in the practice of the invention in monitoring motor oil. In accordance with step 65, the flow-through housing is placed in the oil pan with the associated broad band white light source. The flow-through housing can be inserted through the dipstick port or can be placed in the oil pan as a plug. By controlling the depth at which the housing is placed in the oil pan, the instrument can serve to provide a warning when the oil is low. The broad band white light source can be fixed to the housing in the case of a tungsten filament incandescent lamp or similar lamp that can withstand the hot oil environment. The white light source can also be associated with the housing by providing a fiber optic link from the light source to the housing.

The oil in the flow-through housing is illuminated by the broad band white light source in accordance with step 66. In accordance with step 67, the light transmitted through the oil is received and segregated into optical signals having distinct wavelengths or bandwidths. An optical filter, etalon, or grating, as described previously, can be used to segregate the light into distinct bandwidths.

The optical signals are then converted into proportional electrical signals in accordance with step 69. Additional steps can be included, if necessary, such as improving the signal by methods known to the skilled artisan and amplifying the signal if necessary.

The optical signals are then conveyed to the comparator to determine the concentration of at least one species in the oil, in accordance with step 71. For example, spectral analysis can determine whether the oil is dirty or whether it is contaminated by ethylene glycol. It is then desirable to display an indication of the oil quality to a user in accordance with step 73. The aging process of motor oil and other engine lubricants and fuels can be observed over time using the above device to provide warning if contamination, whether cumulative or catastrophic.

The foregoing description is to be considered illustrative rather than restrictive of the invention. This invention can be used in other contexts for measuring the concentration of species in cooking oil, diesel fuel, hydraulic fluid, brake fluid, antifreeze, gasoline, diesel fuel, and others. Absorbances at various wavelengths will need to be determined empirically for particular species and considered in conjunction with the absorbance pattern of the pure substance in which these species are found. Therefore, it should be understood that the specific embodiment described herein is an illustration of how the present invention may be practiced. Thus modifications that come within the meaning and range of equivalents of the claims are to be included in the foregoing description.

What is claimed is:

1. An instrument for determining the concentration of at least one species in a substance, said instrument comprising:

an instrument housing having a chamber for receiving at least a portion of the substance;

a broad band light source associated with said housing and positioned in illuminating contact with said chamber for illuminating the substance in said chamber;

means for separating the optical signals transmitted through said substance into signals of different wavelengths that are preselected for absorbance by at least one species in the substance and for attenuating light outside the wavelengths transmitted, thereby providing a continuous increase in absorbance as the concentration of the species in the substance increases for any single transmitted wavelength independent of the wavelength for peak absorbance by the species;

means for generating electrical signals from the optical signals that are proportional to the absorbance of the optical signals by the at least one species in the substance; and means electrically connected to said means for generating electrical signals for determining from the electrical signals the concentration of at least one species in the substance in dependence upon the absorbance of the optical signals by the species as light is transmitted through the substance, said means comparing the electrical signals with electrical signals corresponding to the substance in the substantial absence of the species.

2. An instrument according to claim 1 wherein said means for separating the optical signals transmitted through said substance comprises a plurality of optical fibers associated with said housing and positioned in relation to said chamber for receiving light that has been transmitted through the substance, said optical fibers transmitting different preselected wavelengths of light.

3. An instrument according to claim 1 further comprising a display device operatively connected to said concentration determining means for displaying to a user an indication of the concentration of at least one species in the substance.

4. An instrument according to claim 3 wherein said display device is electrically connected to said concentration determining means and includes multiple light emitting diodes for displaying the concentration of the at least one species based on the electrical signals received.

5. An instrument according to claim 1 wherein said concentration determining means comprises an electronic circuit including a multiple channel amplifier for scaling the electrical signals and a microprocessor for receiving the scaled electrical signals, evaluating the signals, and determining the concentration of at least one species based upon the signals.

6. An instrument according to claim 1 wherein said separating means and said means for generating electrical signals proportional to the optical signals is a multiband segmented detector that is physically aligned with the individual fibers of the fiber optic bundle.

7. An instrument for determining the concentration of at least one species in a substance, said instrument comprising:

an instrument housing having a chamber for receiving at least a portion of the substance;

a broad band light source associated with said housing and positioned in illuminating contact with said chamber for illuminating the substance in said chamber;

a plurality of optical fibers associated with said housing and positioned in relation to said chamber for receiving light that has been transmitted through the substance, said optical fibers transmitting different wavelengths of light that are preselected for absorbance by at least one species in the substance and for attenuating light outside the wavelengths transmitted, thereby providing a continuous increase in absorbance as the concentration of the species in the substance increases for any single transmitted wavelength independent of the wavelength for peak absorbance by the species;

means for discriminating among the optical signals transmitted by said optical fibers based upon the wavelengths of the optical signals, wherein said means is operatively connected to said optical fibers;

means for generating electrical signals from the discriminated optical signals that are proportional to the absorbance of the optical signals by the at least one species in the substance; and a comparator electrically connected to said means for generating electrical signals and including means for receiving electrical signals and means for determining from the electrical signals the concentration of at least one species in the substance in dependence upon the absorbance of the optical signals as light is transmitted through the substance by comparing the electrical signals to electrical signals corresponding to the substance in the substantial absence of the species.

8. An instrument according to claim 7 wherein said chamber is a flow-through chamber, the substance is selected from the group consisting of motor oil, cooking oil, hydraulic fluid, diesel fuel, gasoline, and light gaseous and liquid hydrocarbons, and the at least one species is a contaminant.

9. An instrument according to claim 7 wherein said chamber is a flow-through chamber, the substance is selected from the group consisting of motor oil, diesel fuel, and hydraulic fluid, and at least one species is selected from the group consisting of water, ethylene glycol, wear particles, and antioxidants.

10. An instrument according to claim 7 wherein said broad band light source is fixed to said housing opposite said chamber from said optical fibers.

11. An instrument according to claim 7 wherein said housing includes a reflective surface opposite said chamber from said plurality of optical fibers, and wherein said broad band white light source is optically connected to said housing by an optical fiber that transmits a broad band white light and is in illuminating contact with said chamber opposite said reflective surface.

12. An instrument according to claim 7 wherein said light source is a tungsten filament incandescent lamp.

13. An instrument according to claim 7 wherein said plurality of optical fibers transmit preselected wavelengths of light in the range of from about 380 nm to 2500 nm.

14. An instrument according to claim 7 wherein each optical fiber of said plurality of optical fibers transmits a different range of wavelengths of light while attenuating other wavelengths of light.

15. An instrument according to claim 7 wherein at least some of said optical fibers are made of materials selected from the group consisting of silicon rubber, doped glass, and polytetrafluoroethylene.

16. An instrument suitable for determining in situ the concentration of at least one species in a motor oil, said instrument comprising:

an instrument housing having a chamber extending therethrough providing for flow of the oil through said chamber;

a broad band white light source associated with said housing and positioned in illuminating contact with said chamber for illuminating the oil in said chamber;

a plurality of optical fibers associated with said housing and positioned in relation to said chamber for receiving light that has been transmitted through the oil, said optical fibers transmitting wavelengths of light in the range of from about 380 nm to 2500 nm that are preselected for absorbance by at least one species in the oil and attenuating light outside the preselected wavelengths, thereby providing a continuous increase in absorbance as the concentration of the species in the oil increases for any single transmitted wavelength independent of the wavelength for peak absorbance by the species;

a detector operatively connected to said optical fibers and including means for discriminating among the optical signals transmitted by said optical fibers and means for generating electrical signals proportional to the absorbance of the optical signals by the species in the oil;

a comparator electrically connected to said detector and including means for receiving electrical signals from said detector and means for determining the concentration of the species in the oil in dependence upon the absorbance of the optical signal by the oil by comparing the generated electrical signals to electrical signals corresponding to the oil in the substantial absence of the species; and a display device operatively connected to said comparator for displaying to a user an indication of the concentration of at least one species in the oil.

17. A method for determining the concentration of at least one species in a substance, said method comprising the steps of:

a) illuminating the substance with broad band white light;

b) segregating the transmitted light into optical signals having distinct bandwidths within which a species absorbs light and attenuating light outside the distinct bandwidths, thereby providing a continuous increase in absorbance as the concentration of the species in the substance increases for any single transmitted wavelength independent of the wavelength for peak absorbance by the species;

c) converting the optical signals into electrical signals proportional to the absorbance of the optical signals at each of the distinct bandwidths as light is transmitted through the substance;

d) comparing the generated electrical signals to electrical signals corresponding to the substance in the substantial absence of the species; and e) determining the concentration of at least one species in the substance based on the electrical signals.

18. The method of claim 17 wherein the step of converting the optical signals into electrical signals includes the step of discriminating among the optical signals based upon the respective wavelengths of the optical signals.

19. The method of claim 17 wherein the step of determining the concentration of at least one species in the substance comprises amplifying the electronic signals and evaluating the amplified signals to determine the concentration of at least one species.

20. The method of claim 19 wherein the step of evaluating the amplified signals comprises preparing a plot of absorbance versus wavelength and integrating the area under the resulting curve from one wavelength to the next.

21. The method of claim 17 further comprising the step of displaying to a user an indication of the concentration of at least one species in the substance.

22. The method of claim 17 wherein the substance is a fluid and the step of illuminating the substance with a broad band white light source comprises flowing the fluid through a chamber and illuminating the fluid in the chamber.

23. The method of claim 17 wherein the step of segregating the transmitted light into optical signals corresponding to distinct bandwidths comprises receiving the optical signals by and transmitting the optical signals through optical fibers preselected for transmitting light of preselected wavelengths.

24. A method for determining the concentration of at least one species in a fluid, said method comprising the steps of:

a) illuminating the fluid with a broad band white light;

b) segregating the transmitted light into optical signals having distinct bandwidths comprising receiving the optical signals by and transmitting the optical signals through optical fibers preselected for transmitting light of wavelengths absorbed by the species and attenuating light outside the wavelengths transmitted, thereby providing a continuous increase in absorbance as the concentration of the species in the fluid increases for any single transmitted wavelength independent of the wavelength for peak absorbance by the species;

c) converting the optical signals into electrical signals proportional to the absorbance of the optical signals as light is transmitted through the fluid;

d) preparing a plot of absorbance versus wavelength and integrating the area under the resulting curve from one wavelength to the next;

e) comparing the integral obtained from step d) with that for a fluid in the substantial absence of the species;

f) determining an indication of the concentration of at least one species in the fluid based on the comparison from step e); and g) displaying to a user an indication of the concentration of at least one species in the fluid.

25. A method for determining the quality of motor oil, said method comprising the steps of:

a) illuminating the motor oil with a broad band white light source;

b) filtering the light transmitted through the motor oil into optical signals of distinct bandwidth that are preselected for absorbance by contaminants in the motor oil and attenuating light outside the distinct bandwidth, thereby providing a continuous increase in absorbance as the contaminants in the motor oil increase for any single transmitted wavelength independent of the wavelength for peak absorbance by the contaminants;

c) converting the optical signals into electrical signals that are proportional to the absorbance of the light by the contaminants;

d) comparing the electrical signal to one for reference motor oil to determine the quality of the oil based upon the electrical signal; and e) displaying to a user an indication of the quality of the motor oil.

26. The method of claim 25 wherein the step of displaying to a user an indication of the quality of the motor oil is performed continuously.

* * * * *